United States Patent [19]

Adam et al.

[11] Patent Number: 5,710,258
[45] Date of Patent: Jan. 20, 1998

[54] AZO DYES

[75] Inventors: Jean-Marie Adam, Rosenau, France; Peter Sutter, Muttenz, Switzerland

[73] Assignee: Ciba Specialty Chemicals Corporation, Tarrytown, N.Y.

[21] Appl. No.: 595,435

[22] Filed: Feb. 5, 1996

[30] Foreign Application Priority Data

Feb. 10, 1995 [CH] Switzerland ................. 406/95

[51] Int. Cl.⁶ .................. C09B 62/62; C09B 62/665; C09B 62/82; D06P 1/38
[52] U.S. Cl. .................. 534/643; 8/543; 8/680; 8/693; 534/640; 534/730; 534/731; 534/804
[58] Field of Search .................. 534/643, 730, 534/731, 804, 640; 8/543, 680, 693

[56] References Cited

U.S. PATENT DOCUMENTS

| | | | |
|---|---|---|---|
| 2,849,437 | 8/1958 | de Montmollin et al. | 260/196 |
| 3,136,752 | 6/1964 | Jung et al. | 260/162 |
| 4,249,275 | 2/1981 | Hugl et al. | 534/730 X |
| 4,339,380 | 7/1982 | Hugl et al. | 534/730 |
| 4,382,890 | 5/1983 | De Montmollin et al. | 534/643 |
| 5,092,903 | 3/1992 | Miemann | 534/643 |

FOREIGN PATENT DOCUMENTS

| | | |
|---|---|---|
| 0028351 | 5/1981 | European Pat. Off. |
| 0984802 | 3/1965 | United Kingdom |
| 1037648 | 8/1966 | United Kingdom |
| 1039928 | 8/1966 | United Kingdom |
| 1252453 | 11/1971 | United Kingdom |

OTHER PUBLICATIONS

Chemical Abstract, 95:99322c.

*Primary Examiner*—Floyd D. Higel
*Attorney, Agent, or Firm*—David R. Crichton; Kevin T. Mansfield

[57] ABSTRACT

The invention relates to compounds of formula

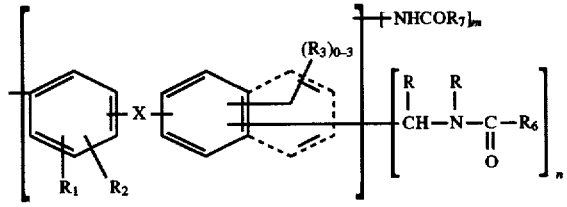

The compounds of formula (1) are suitable as dye for dyeing or printing hydroxyl group-containing or nitrogen-containing fibre materials and give dyeings of prints having good allround fastness properties.

13 Claims, No Drawings

AZO DYES

The present invention relates to novel azo dyes, to processes for their preparation as well as to the use thereof for dyeing fibre materials from an aqueous bath or for printing fibre materials.

Accordingly, this invention relates to compounds of formula

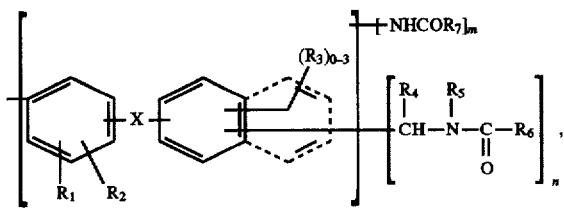

(1)

wherein K is the radical of a coupling component of the benzene or naphthalene series or of the heterocyclic series, X is a bridge member of formula —$SO_2$—O—, —$SO_2$—N($R_8$)—, —COO— or —CO—N($R_9$)—, wherein $R_8$ and $R_9$ are each independently of the other hydrogen or $C_1$–$C_4$alkyl, $R_1$ and $R_2$ are each independently of the other hydrogen, $C_1$–$C_4$alkyl, $C_1$–$C_4$alkoxy, halogen or sulfo, $(R_3)_{0-3}$ is 0–3 identical or different radicals $R_3$ selected from the group consisting of $C_1$–$C_4$alkyl, $C_1$–$C_4$alkoxy, halogen and sulfo, $R_4$ is hydrogen, carboxyl or trihalomethyl, $R_5$ is hydrogen or $C_1$–$C_4$alkyl, $R_6$ is unsubstituted or substituted $C_1$–$C_4$alkyl, $C_2$–$C_4$alkenyl or phenyl, or the —N($R_5$)—CO—$R_6$ radical is a radical of formula

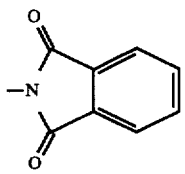

(2)

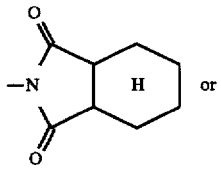

or (3)

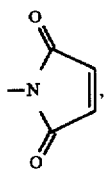

(4)

$R_7$ is a —CHY—$CH_2$Y or —CY=$CH_2$ radical, wherein Y is bromo or chloro, m is 0 or 1, and n is 0, 1, 2 or 3, with the proviso that the sum of (n+m)≧1.

The coupling components K-H on which the compounds of formula (1) are based are per se known and have been very widely described, e.g. in Venkataraman "The Chemistry of Synthetic Dyes" volume 6, pages 213–297, Academic Press, New York, London 1972.

K is preferably the radical of a benzene, naphthalene, pyrazolone, aminopyrazole, pyridone, pyrimidine, indole, naphthylimidazole, diphenylamine, pyrazolo[2,3-a] pyrimidine, tetrahydroquinoline or aceto acetic acid amide coupling component, which radicals can be further substituted.

Suitable substituents attached at the radical K are typically $C_1$–$C_6$alkyl, which will generally be understood to mean methyl, ethyl, n- or iso-propyl, n-, iso-, sec- or tert-butyl, or straight-chain or branched pentyl or hexyl; $C_1$–$C_4$alkoxy, which will generally be understood to mean methoxy, ethoxy, n- or iso-propoxy or n-, iso-, sec- or tert-butoxy; phenoxy; unsubstituted or hydroxy-substituted $C_2$–$C_6$alkanoylamino, typically acetylamino, hydroxyacetylamino or propionylamino; benzoylamino; amino; N-$C_1$–$C_4$alkylamino or N,N-di-$C_1$–$C_4$alkylamino, each of which is unsubstituted or substituted in the alkyl moiety by e.g. hydroxy, $C_1$–$C_4$alkoxy, carboxy, cyano, halogen, sulfo, sulfato, phenyl or sulfophenyl, typically methylamino, ethylamino, N,N-dimethylamine, N,N-diethylamino, β-cyanoethylamino, β-hydroxyethylamino, N,N-di-β-hydroxyethylamino, β-sulfoethylamino, γ-sulfo-n-propylamino, β-sulfoethylamino, N-ethyl-N-(β-sulfobenzyl)amino, N-(β-sulfoethyl)-N-benzylamino; cyclohexylamino; N-phenylamino or N-$C_1$–$C_4$alkyl-N-phenylamino, each of which is unsubstituted or substituted in the phenyl moiety by $C_1$–$C_4$alkyl, $C_1$–$C_4$alkoxy, halogen or sulfo; $C_2$–$C_4$alkoxycarbonyl, typically methoxycarbonyl or ethoxycarbonyl; trifluoromethyl; nitro; cyano; halogen, which will generally be understood to mean fluoro, bromo or, preferably, chloro; ureido; hydroxy; carboxy; sulfo; sulfomethyl; carbamoyl; sulfamoyl; N-phenylsulfamoyl or N-$C_1$–$C_4$alkyl-N-phenylsulfamoyl, each of which is unsubstituted or substituted in the phenyl moiety by sulfo or carboxy; methylsulfonyl or ethylsulfonyl; or phenylazo or naphthylazo, each of which is unsubstituted or substituted by e.g. $C_1$–$C_4$alkyl, $C_1$–$C_4$alkoxy, halogen, sulfo, amino, N-$C_1$–$C_4$alkylamino, N,N-di-$C_1$–$C_4$alkylamino, or phenylamino.

Preferred meanings of K are: a phenyl or naphthyl radical carrying one or more than one substituent selected from the group consisting of sulfo, hydroxy, $C_1$–$C_4$alkoxy, amino, N-$C_1$–$C_4$alkylamino or N,N-di-$C_1$–$C_4$alkylamino, acetylamino, benzoylamino, $C_1$–$C_4$alkyl; and phenylazo or nephthylazo, each of which is unsubstituted or substituted by $C_1$–$C_4$alkyl, $C_1$–$C_4$alkoxy, halogen, sulfo, amino, N-$C_1$–$C_4$alkylamino, N,N-di-$C_1$–$C_4$alkylamino, or phenylamino a 1-phenylpyrazol-5-one or 1-phenyl-5-aminopyrazole radical, each of which is unsubstituted or substituted by $C_1$–$C_4$alkyl, $C_1$–$C_4$alkoxy, sulfo or halogen; an indole radical which is unsubstituted or substituted by $C_1$–$C_4$alkyl, $C_1$–$C_4$alkoxy, sulfo or halogen; and a naphthylimidazole radical which is unsubstituted or substituted by $C_1$–$C_6$alkyl, sulfo, hydroxy or phenylamino, which phenylamino can in turn be substituted by $C_1$–$C_4$alkyl, $C_1$–$C_4$alkoxy, sulfo or halogen.

K is particularly preferably a 1- or 2-naphthyl radical carrying one or more than one substituent selected from the group consisting of hydroxy, amino, acetylamino, sulfo and chloro, or a 1-phenyl-pyrazol-5-one or 1-phenyl-5-aminopyrazole radical, each of which carries one or more than one substituent selected from the group consisting of methyl, methoxy, sulfo and chloro.

$R_1$ and $R_2$ are each independently of the other preferably hydrogen, methyl, ethyl, methoxy, ethoxy, chloro or sulfo and, most preferably, hydrogen, methyl, methoxy, chloro or sulfo. A particularly preferred embodiment of the invention relates to compounds of formula (1), wherein $R_1$ is hydrogen, and $R_2$ is hydrogen, methyl, methoxy, chloro or sulfo.

$(R_3)_{0-3}$ is preferably 0 to 3 identical or different radicals selected from the group consisting of methyl, ethyl, methoxy, ethoxy, chloro or sulfo and, most preferably, those selected from the group consisting of methyl, methoxy, chloro or sulfo. A particularly preferred embodiment of the invention relates to compounds of formula (1), wherein $(R_3)_{0-3}$ is 0 to 3 methyl radicals.

The bridge members X cited in formula (1) will be understood to be such that their S or C atom is attached at the left phenyl radical carrying $R_1$ and $R_2$, and the O or N atom is attached at the right phenyl or naphthyl radical carrying the $(R_3)_{0-3}$ group. X is preferably a bridge member of formula $—SO_2O—$, $—SO_2—N(C_1-C_4\text{alkyl})—$, $—COO—$ or $—CO—N(C_1-C_4\text{alkyl})—$. X is most preferably the $—SO_2—O—$ group.

$R_4$ is preferably hydrogen, carboxyl or trifluoromethyl. Hydrogen is particularly preferred.

$R_5$ is preferably hydrogen, methyl or ethyl. Hydrogen is particularly preferred.

$R_6$ defined as unsubstituted or substituted $C_1-C_4$alkyl is typically unsubstituted or halogen-substituted $C_1-C_4$alkyl. $R_6$ defined as unsubstituted or substituted $C_1-C_4$alkyl is preferably an unsubstituted $C_1-C_4$alkyl radical or, more preferably, a $—CH_2Y$ or $—CHY—CH_2Y$ radical, wherein Y is bromo or chloro. $R_6$ defined as unsubstituted or substituted $C_1-C_4$alkyl is most preferably a radical of formula $—CH_2Cl$ or $—CHBr—CH_2Br$.

$R_6$ defined as unsubstituted or substituted $C_2-C_4$alkenyl may be, for example, a $—CH=CH_2$ group or, preferably, a $—CY_1=CH_2$ group, wherein $Y_1$ is halogen, typically chloro or bromo. $R_6$ defined as unsubstituted or substituted $C_2-C_4$alkenyl is preferably a $—CBr=CH_2$ radical.

$R_6$ defined as unsubstituted or substituted phenyl is typically phenyl which is unsubstituted or substituted by $C_1-C_4$alkyl, $C_1-C_4$alkoxy, halogen or sulfo and, preferably, unsubstituted phenyl.

Particularly preferred meanings of $R_6$ are: $C_1-C_4$alkyl; a $—CH_2Y$ or $—CHY—CH_2Y$ radical, wherein Y is bromo or chloro; a $—CH=CH_2$ or $—CY_1=CH_2$ group, wherein $Y_1$ is chloro or bromo; or phenyl. $R_6$ is most preferably a $—CH_2Cl$, $—CHBr—CH_2Br$ or $CBr=CH_2$ radical.

$R_7$ is preferably the $—CHBr—CH_2Br$ or $—CBr=CH_2$ radical.

m is preferably 0. n is preferably 1 or 2. The sum of (n+m) is preferably 1 or 2. Particularly preferred compounds of formula (1) are those wherein m is 0, and n is 1 or 2. Other preferred compounds of formula (1) are those wherein m is 1, and n is 0.

A preferred embodiment of the invention relates to compounds of formula

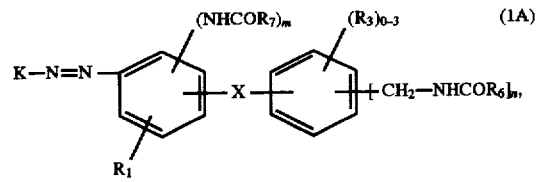

(1A)

wherein K has the meanings and preferred meanings given above, X is a bridge member $—SO_2—O—$, $R_1$ is hydrogen, methyl, ethyl, methoxy, ethoxy, chloro or sulfo, $(R_3)_{0-3}$ is 0 to 3 identical or different radicals selected from the group consisting of methyl, ethyl, methoxy, ethoxy, chloro or sulfo, $R_6$ is $C_1-C_4$alkyl, a $—CH_2Y$ or $—CHY—CH_2Y$ radical, wherein Y is bromo or chloro, a $—CH=CH_2$ or $—CY_1=CH_2$ group, wherein $Y_1$ is chloro or bromo, or phenyl, $R_7$ is the $—CHBr—CH_2Br$ or $—CBr=CH_2$ radical, and m is 0 or 1, and n is 0, 1 or 2, the sum of (n+m) being $\geq 1$.

A particularly preferred embodiment of this invention relates to compounds of the above formula (1A), wherein K is a 1- or 2-naphthyl radical carrying one or more than one substituent selected from the group consisting of hydroxy, amino, acetylamino, sulfo and chloro, or a 1-phenyl-pyrazol-5-one- or 1-phenyl-5-aminopyrazole radical, each of which carries one or more than one substituent selected from the group consisting of methyl, methoxy, sulfo and chloro, X is a bridge member $—SO_2—O—$, $R_1$ is hydrogen, methyl, methoxy, chloro or sulfo, $(R_3)_{1-3}$ is 0 to 3 identical or different radicals selected from the group consisting of methyl, methoxy, chloro or sulfo, $R_6$ is a $—CH_2Cl$, $—CHBr—CH_2Br$ or $CBr=CH_2$ radical, and m is 0, and n is 1 or 2.

The compounds of formula (1) contain one or more than one sulfo group which is either in the form of the free sulfonic acid thereof or, preferably, in the form of salts thereof. Suitable salts are typically the alkali metal salts or the alkaline earth metal salts, the ammonium salt, or salts of organic amines. Illustrative examples are the sodium, potassium, lithium or ammonium salts, the salts of the mono-, di- or triethanolamine, or mixtures thereof. The preferred compounds of formula (1) contain one sulfo group.

The compounds of formula (1) can be prepared, for example, by diazotising an amine of formula

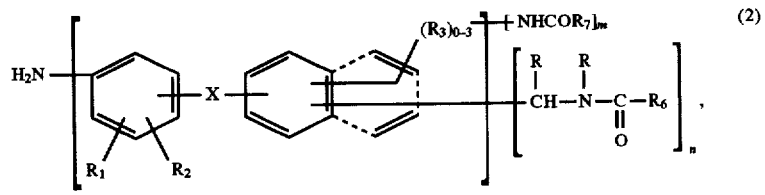

(2)

wherein $R_1$, $R_2$, $(R_3)_{0-3}$, $R_4$, $R_5$, $R_6$, $R_7$, X, n and m each have the meaning given above, and coupling the diazonium compound so obtained with a coupling component of formula

K-H (3), wherein K has the meaning given above. The amines of formula (2) can be diazotised in conventional manner, typically using nitrites such as sodium nitrite in acid medium, e.g. in a medium containing hydrochloric acid, typically at 0°–15° C. The coupling of the diazotised amines of formula (2) with the coupling component of formula (3) is preferably carried out in an aqueous or aqueous-organic medium in the temperature range from typically 0°–30° C. and at a neutral or weakly acidic pH.

The compounds of formula (2) are novel and constitute a further object of the invention. They can typically be obtained by reacting a compound of formula

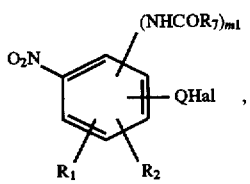

(4)

or a corresponding compound containing a precursor of the —(NHCOR₇)ₘ₁ radical, with a compound of formula

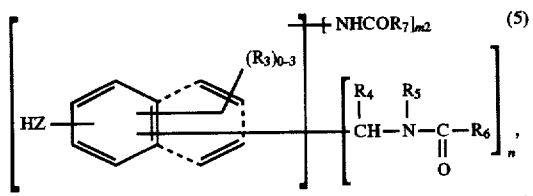

(5)

or with a corresponding compound containing a precursor of the —(NHCOR₇)$_{m2}$ and/or —(CHR₄—NR₅—COR₆)$_n$ radical, and then converting the nitro compound so obtained, typically by catalytic hydrogenation, into the corresponding amine and, where precursors of the compounds of formula (4) and/or (5) are used, converting these into the final compounds, wherein $R_1$, $R_2$, $(R_3)_{1-3}$, $R_4$, $R_5$, $R_6$, $R_7$ and n each have the meaning given above, -QHal is typically the —COCl or —SO₂Cl radical, —ZH is a —OH or —NH(R₈) radical, wherein $R_6$ has the meaning given above, and m1 and m2 are each 0 or 1, the sum of (m1+m2) being 0 or 1.

The reaction of the compounds of formulae (4) and (5) can be carried out in conventional manner, e.g. in aqueous or organic medium in the presence of a base and at elevated temperature. The catalytic hydrogenation can also be carded out under the usual conditions, typically using a Pd/C catalyst or Raney nickel in an organic solvent, e.g. in tetrahydrofuran or dimethylformamide. If the compound of formula (4) in this process is replaced with a suitable precursor, then said precursor can be, for example, a compound containing instead of the —(NHCOR₇)$_{m1}$ group a substituent which can be converted into an amino group, typically chloro or nitro, and which can be reacted, after its conversion into the amino group, with e.g a Cl—COR₇ compound. If the compound of formula (5) in this process is replaced with a suitable precursor, then said precursor can be, for example, a compound containing instead of the —(CHR₄—NR₅—COR₆)$_n$ group a —(CH₂R₄)$_n$ group which can then be converted into by final compound, typically by the Einhorn reaction.

The compounds of formulae (4) and (5) and corresponding precursors thereof are known or can be prepared by known methods.

The novel compounds of formula (1) are suitable as dyes for dyeing and printing a very wide range of fibre materials, such as hydroxyl group-containing or nitrogen-containing fibre materials. Typical examples of such fibre materials are the natural cellulose fibres such as cotton, linen, jute or hemp, as well as modified cellulose fibre materials such as pulp or regenerated cellulose. The compounds of formula (1) are particularly suitable as dyes for dyeing or printing natural polyamide fibre materials, typically silk or wool, synthetic polyamide fibre materials, e.g. polyamide 6 or polyamide 6.6, or blends of wool with synthetic polyamide. In particular, the compounds of formula (1) are suitable dyes for dyeing or printing natural polyamide fibre materials, preferably wool.

The cited textile fibre material can be in any form of presentation, typically fibres, yarns, flock, wovens or knitgoods.

The novel dyes of formula (1) are suitable for the conventional dyeing and printing processes and may be applied to and fixed on the fibre matedal in different manner, preferably in the form of aqueous dye solutions and printing pastes. The novel dyes of formula (1) are suitable both for the exhaust process and for dyeing by the pad dyeing process, in which the goods are impregnated with aqueous and, where appropriate, salt-containing, dye solutions, and the dyes are fixed after treatment with alkali, or in the presence of alkali, with or without the application of heat. The novel dyes of formula (1) are also suitable for the so-called cold pad-batch method, which comprises applying the dye together with the alkali on the pad and subsequently fixing the dye by storing the impregnated goods for several hours at room temperature.

The dyeing of natural and synthetic polyamide fibre materials, in particular of wool, is preferably carded out by the exhaust process at a pH of c. 3 to 7, preferably 3 to 5, and in the temperature range from e.g. 70° to 110° C. and, preferably, from 90° to 100° C.

In addition to water and the dyes, the dyeing liquors or printing pastes may contain further auxiliaries, typically salts, buffer substances, wetting agents, antifoams, levelling agents or agents influencing the properties of the textile material, such as softeners, auxiliaries for the provision of a flame retarding finishing, or dirt, water and oil repellents as well as water softeners, and natural or synthetic thickeners, typically alginates or cellulose ethers.

The dyeings and prints obtained with the novel dyes of formula (1) are level and have good allround fastness properties, in particular good fastness to washing, rubbing, wet treatments, wet-rubbing and light. The dyes of formula (1) are also distinguished by uniform colour build-up, good fibre affinity, high degree of fixation as well as good compatibility with other dyes. Furthermore, when the novel dyes of formula (1) are used the usual after-treatment of the dyeings and prints with the so-called fixing agents can be dispensed with.

In the following Examples, parts are parts by weight. The ratio of parts by weight and parts by volume is the same as that of the gram to the cubic centimeter.

Example 1: 30.3 parts of o-cresol are dissolved in a medium consisting of 112 parts of water, 37.1 parts of concentrated sodium hydroxide solution and 2.8 parts of sodium carbonate. This solution is heated to 80° C. and then 71.1 parts of 2-chloro-5-nitrobenzene-1-sulfochloride are added and the mixture is stirred for c. 2.5 hours at this temperature. After cooling this mixture to room temperature, the precipitated solids are isolated by filtration, washed with water and methanol and then dried, giving 84.2 parts of the compound of formula

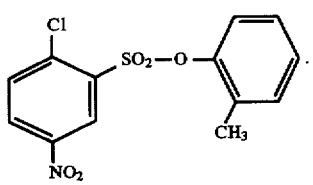

(6)

82 parts of the compound of formula (6) are stirred in an autoclave with 150 parts of ethanol and 100 parts of 25% ammonia for 10 hours at 110° C. The emulsion so obtained is diluted with 50 parts of water and the solids are then isolated by filtration, washed neutrally and dried, giving 67 parts of the compound of formula

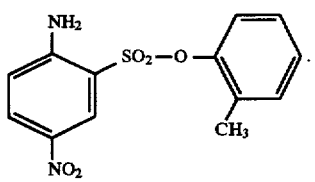
(7)

66.3 parts of the compound of formula (7) are hydrogenated catalytically with 5% Pd/C in 500 parts of tetrahydrofuran. The reaction mixture is concentrated by evaporation, giving 59.1 parts of the diamine of formula

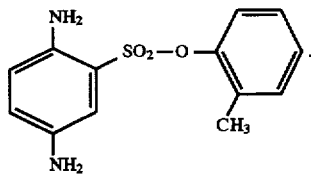
(8)

22.3 parts of the diamine of formula (8) are dissolved in 60 parts of acetone, and to this solution are added 16 parts of sodium acetate. After the the addition of 21.2 parts of dibromopropionyl chloride at 0°–5° C., the mixture is stirred for 1 hour and 40 parts of water are then added. The organic phase is then isolated, diluted with 150 parts of ether and dried over sodium sulfate. The mixture is clarified by filtration, the filtrate is saturated cold with Hcl gas, and the precipitated hydrochloride of formula

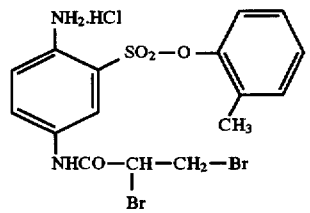
(9)

is then isolated by filtration and dried.

5.3 parts of the compound of formula (9) are dissolved in 25 parts of sulfolane, and to this solution are added dropwise 3.3 parts of nitrosyl sulfuric acid at c. 12° C. After 1 hour, the diazo solution is poured on 80 parts of ice/water, and 2.6 parts of 5-amino-3-methyl-1-(3-sulfophenyl)pyrazole are then added at 0°–5° C. After a further 3 hours, the reaction mixture is adjusted to pH 2 with sodium acetate solution and the reaction is allowed to go to completion overnight. The pH of the yellow solution is then adjusted to 7.5 and the dye is salted out with sodium chloride, isolated by filtration and dried, giving the compound of formula

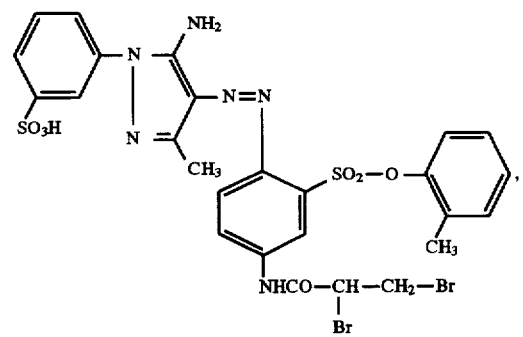

which dyes wool in a yellow shade having good allround fastness properties.

Example 2–3: The compounds of formulae

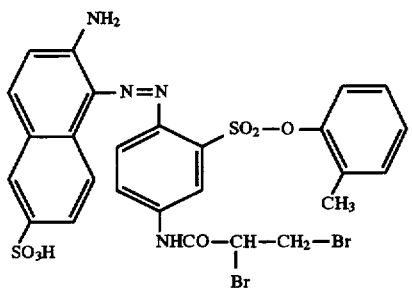
2 and

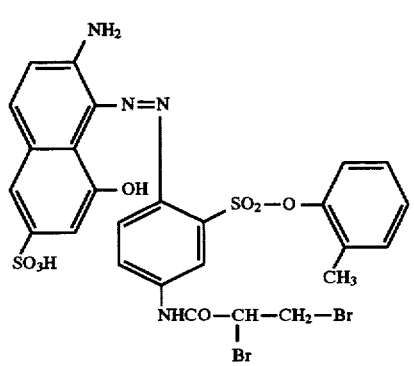
3 can be prepared in general accordance with the procedure of Example 1.

Example 4: 108 parts of p-cresol and 250 parts of N-hydroxymethylchloroacetamide added to 500 parts of 98% sulfuric acid at 0°–20° C. The reaction is allowed to go to completion overnight and the reaction mixture is then poured on 1500 parts of ice and the compound of formula

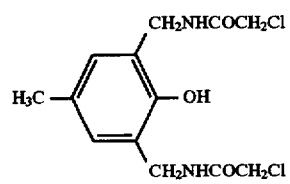
(10)

is isolated by filtration and then washed and dried in conventional manner.

19.2 parts of the compound of formula (10) are dissolved in 250 parts of acetone, and to this solution are added 6.1 parts of triethylamine. To this mixture is then added dropwise over 5 minutes a solution of 13.3 parts of 2-nitrobenzene-1-sulfochloride in 50 parts of acetone, and the entire mixture is then refluxed for 15 minutes and evaporated to dryness. The residue is stirred in 300 parts of water and the solids are isolated by filtration. The solids are then boiled in c. 300 parts of methanol, isolated once more by filtration and dried, giving 24 parts of the compound of formula

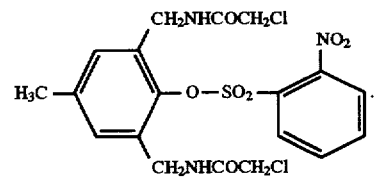
(11)

5.1 parts of the compound of formula (11) are hydrogenated catalytically with 0.5 parts of 5% Pd/C and the reaction mixture is then concentrated by evaporation, giving 4.4 parts of the compound of formula

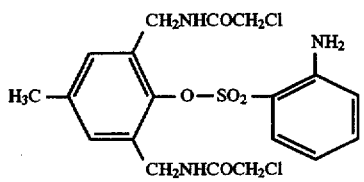
(12)

9.5 parts of the compound of formula (12) are dissolved in 45 parts of glacial acetic acid, 11 parts of concentrated Hcl and 11 parts of water and then diazotised with the addition of 5.1 parts of 4N sodium nitrite solution at 0°–5° C. To this mixture are added 10.5 parts of sodium acetate (pH 2.5) and subsequently 5.3 parts of 5-amino-3-methyl-1-(3-sulfophenyl)pyrazole are added at 0°–5° C. The mixture is stirred for 3 hours at room temperature and then poured on 120 parts of 25% solution of sodium chloride. The liquid phase is decanted off and the residue is dissolved in 200 parts of water. The pH is adjusted to 7.5 with sodium hydroxide solution and the dye is salted out with sodium chloride, isolated by filtration and dried, giving the dye of formula

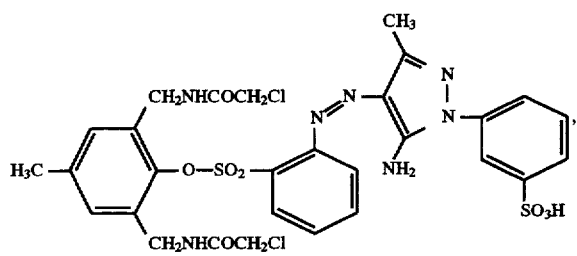

which dyes wool in a yellow shade having good allround fastness properties.

The following dyes can be prepared in general accordance with the procedure of Example 4.

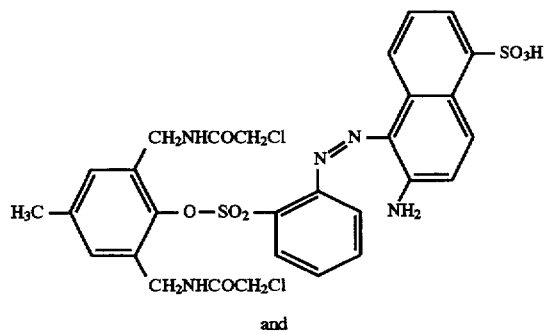

and

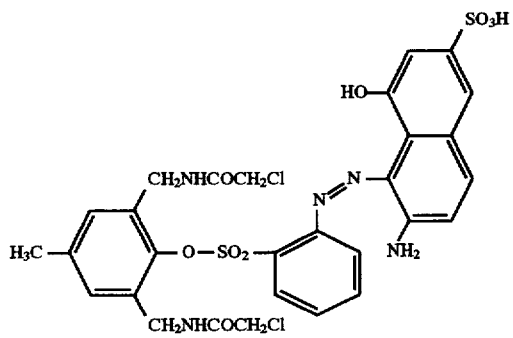

Examples 7–9: 139 parts of mesitol are dissolved in 1200 parts of acetone, and to this solution are added 117 parts of triethylamine. To this mixture is added dropwise over 20 minutes a solution of 267 parts of 2-nitrobenzene-1-sulfochloride in 600 parts of acetone, and the entire mixture is refluxed for 1 hour and then evaporated to dryness. The residue is stirred in water and the solids are isolated by filtration. These solids are dissolved hot in c. 700 parts of acetone, and subsequently 500 parts of acetone are distilled off and 500 parts of methanol are added. The precipitated solids are then again isolated by filtration and dried, giving 209 parts of the compound of formula

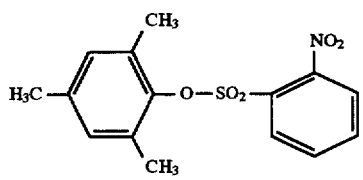
(13)

161 parts of the compound of formula (13) are hydrogenated catalytically using Raney nickel at elevated temperature (60°) and under pressure (40 bar). The reaction mixture is then concentrated by evaporation, giving 142 parts of the compound of formula

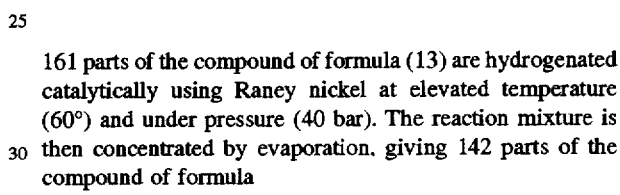
(14)

58.3 parts of the compound of formula (14) and 50.4 parts of N-hydroxymethylchloroacetamide are homogenised and then added to 110 parts of 98% sulfuric acid at 0°–5° C. After 4 hours, this mixture on 1000 parts of ice, and the precipitate is then isolated by filtration, washed neutrally and dried, giving 81 parts of the compound of formula

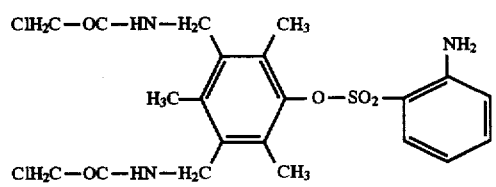

This compound is used, in general accordance with the procedure of Example 4, to prepare the dyes of formulae

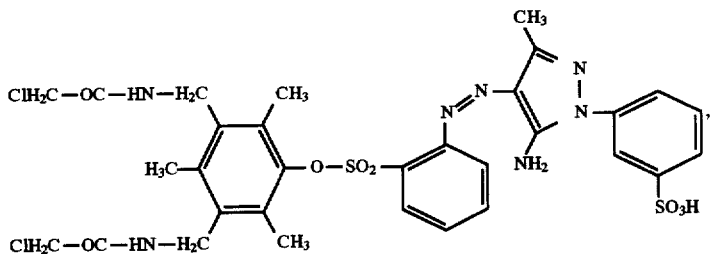

7

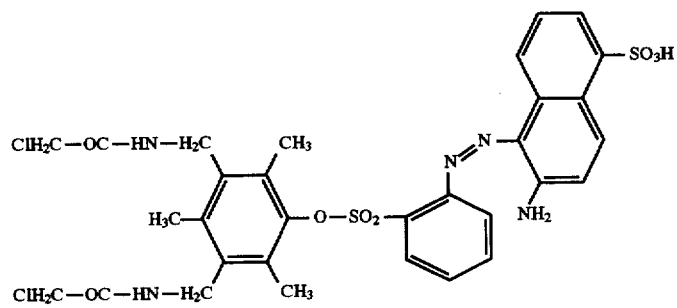

8 and

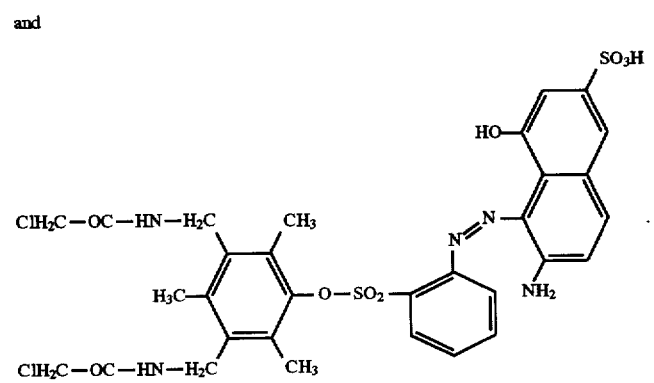

9

Dyeing Instruction: 100 parts of a wool fabric are pretreated for 5 minutes at 30° C. and pH 4.5 in an aqueous bath containing 4000 parts of water, 5 parts of sodium sulfate, 1.5 parts of a levelling agent, 8 parts of sodium acetate and 8 parts of 80% acetic acid. After adding an aqueous solution containing 1.2 parts of the dye of Example 1, the dye liquor is kept for a further 5 minutes at 30° C. and then heated to 100° C. at a heating rate of 1° C. per minute. Dyeing is carded out for 60 minutes at this temperature and the batch is then cooled to 50° C. and the dye liquor is drained. The wool fabric dyed in a yellow shade is then washed and dried in conventional manner. The dyeing obtained is level and and has good allround fastness properties.

What is claimed is:

1. A compound of formula

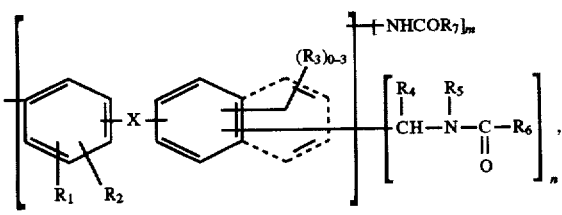

(1)

wherein K is the radical of a benzene, naphthalene, 1-phenypyrazol-5-one, 1-phenyl-5-aminopyrazole, pyridone, pyrimidine, indole, naphthylimidazole, diphenylamine, pyrazolo[2,3-a]pyrimidine, tetrahydroquinoline or aceto acetic acid amide coupling component, which radicals are unsubstituted or substituted by $C_1$–$C_6$alkyl; $C_1$–$C_4$alkoxy; phenoxy; unsubstituted or hydroxy-substituted $C_2$–$C_6$alkanoylamino; benzoylamino; amino; N-$C_1$–$C_4$alkylamino or N,N-di-$C_1$–$C_4$alkyamino, each of which is unsubstituted or substituted in the alkyl moiety by hydroxy, $C_1$–$C_4$alkoxy, carboxy, cyano, halogen, sulfo, sulfato, phenyl or sulfophenyl; cyclohexylamino; N-phenylamino or N-$C_1$–$C_4$alkyl-N-phenylamino, each of which is unsubstituted or substituted in the phenyl moiety by $C_1$–$C_4$alkyl, $C_1$–$C_4$alkoxy, halogen or sulfo; $C_2$–$C_4$alkoxycarbonyl; trifluromethyl; nitro; cyano; halogen, ureido; hydroxy; carboxy; carboxy; sulfo; sulfomethyl; carbamoyl; sulfamoyl; N-phenylsulfamoyl or N-$C_1$–$C_4$alkyl-N-phenylsulfamoyl; each of which is unsubstituted or substituted in the phenyl moiety by sulfo or carboxy; methylsulfonyl or ethylsulfonyl; or phenylazo or naphthylazo, each of which is unsubstituted or substituted by $C_1$–$C_4$alkyl, $C_1$–$C_4$alkoxy, halogen, sulfo, amino, N-$C_1$–$C_4$alkylamino, N,N-di-$C_1$–$C_4$alkylamino, or phenylamino; X is a bridge member of formula —$SO_2$—O—, $R_1$ and $R_2$ are each independently of the other hydrogen, $C_1$–$C_4$alkyl, $C_1$–$C_4$alkoxy, halogen or sulfo, $(R_3)_{0-3}$ is 0–3 identical or different radicals $R_3$ selected from the group consisting of $C_1$–$C_4$alkyl, $C_1$–$C_4$alkoxy, halogen and sulfo, $R_4$ is hydrogen, carboxyl or trihalomethyl, $R_5$ is hydrogen or $C_1$–$C_4$alkyl, $R_6$ is unsubstituted or substituted $C_1$–$C_4$alkyl, $C_2$–$C_4$alkenyl or phenyl, or the —N($R_5$)—CO—$R_6$ radical is a radical of formula (2)

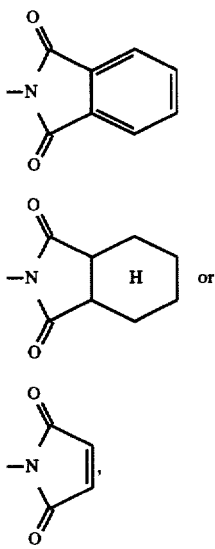

(3)

(4)

$R_7$ is a —CHY—CH$_2$Y or —CY=CH$_2$ radical, wherein Y is bromo or chloro, m is 0 or 1, and n is 0, 1, 2 or 3, with the proviso that the sum of (n+m) ≧ 1.

2. A compound according to claim 1, wherein K is a phenyl or naphthyl radical carrying one or more than one substituent selected from the group consisting of sulfo, hydroxy, $C_1$-$C_4$alkoxy, amino, N-$C_1$-$C_4$alkylamino or N,N-di-$C_1$-$C_4$alkylamino, acetylamino, benzoylamino, $C_1$-$C_4$alkyl; and phenylazo or naphthylazo, each of which is unsubstituted or substituted by $C_1$-$C_4$alkyl, $C_1$-$C_4$alkoxy, halogen, sulfo, amino, N-$C_1$-$C_4$alkylamino, N,N-di-$C_1$-$C_4$alkylamino, or phenylamino; a 1-phenylpyrazol-5-one or 1-phenyl-5-aminopyrazole radical, each of which is unsubstituted or substituted by $C_1$-$C_4$alkyl, $C_1$-$C_4$alkoxy, sulfo or halogen; an indole radical which is unsubstituted or substituted by $C_1$-$C_4$alkyl, $C_1$-$C_4$alkoxy, sulfo or halogen; or a naphthylimidazole radical which is unsubstituted or substituted by $C_1$-$C_6$alkyl, sulfo, hydroxy or phenylamino, which phenylamino is unsubstituted or substituted by $C_1$-$C_4$alkyl, $C_1$-$C_4$alkoxy, sulfo or halogen.

3. A compound according to claim 1, wherein K is a 1- or 2-naphthyl radical carrying one or more than one substituent selected from the group consisting of hydroxy, amino, acetylamino, sulfo and chloro, or a 1-phenyl-pyrazol-5-one or 1-phenyl-5-aminopyrazole radical, each of which carries one or more than one substituent selected from the group consisting of methyl, methoxy, sulfo and chloro.

4. A compound according to claim 1, wherein $R_1$ and $R_2$ are each independently of the other hydrogen, methyl, ethyl, methoxy, ethoxy, chloro or sulfo.

5. A compound according to claim 1, wherein $(R_3)_{0-3}$ is 0 to 3 identical or different radicals selected from the group consisting of methyl, ethyl, methoxy, ethoxy, chloro and sulfo.

6. A compound according to claim 1, wherein m is 0 and n is 1 or 2, and $R_6$ is $C_1$-$C_4$alkyl; a —CH$_2$Y or —CHY—CH$_2$Y radical, wherein Y is bromo or chloro; a —CH=CH$_2$ or —CY$_1$=CH$_2$ group, wherein Y$_1$ is chloro or bromo; or phenyl.

7. A compound according to claim 6, wherein $R_6$ is the —CH$_2$Cl, —CHBr—CH$_2$Br or —CBr=CH$_2$ radical.

8. A compound according to claim 1, of formula

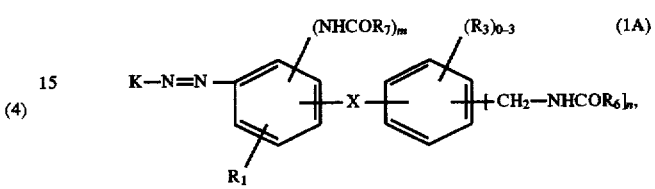

(1A)

wherein K is as claimed in claim 1, X is a bridge member —SO$_2$—O—, $R_1$ is hydrogen, methyl, ethyl, methoxy, ethoxy, chloro or sulfo, $(R_3)_{0-3}$ is 0 to 3 identical or different radicals selected from the group consisting of methyl, ethyl, methoxy, ethoxy, chloro or sulfo, $R_6$ is $C_1$-$C_4$alkyl, a —CH$_2$Y or —CHY—CH$_2$Y radical, wherein Y is bromo or chloro, a —CH=CH$_2$ or —CY$_1$=CH$_2$ group, wherein Y$_1$ is chloro or bromo, or phenyl, $R_7$ is the —CHBFCH$_2$Br or —CBr=CH$_2$ radical, and m is 0 or 1, and n is 0, 1 or 2, the sum of (n+m) being ≧1.

9. A compound according to claim 8 of formula (1A), wherein K is a 1- or 2-naphthyl radical carrying one or more than one substituent selected from the group consisting of hydroxy, amino, acetylamino, sulfo and chloro, or a 1-phenyl-pyrazol-5-one- or 1-phenyl-5-aminopyrazole radical, each of which carries one or more than one substituent selected from the group consisting of methyl, methoxy, sulfo and chloro, X is a bridge member —SO$_2$—O—, $R_1$ is hydrogen, methyl, methoxy, chloro or sulfo, $(R_3)_{0-3}$ is 0 to 3 identical or different radicals selected from the group consisting of methyl, methoxy, chloro or sulfo, $R_6$ is a —CH$_2$Cl, —CHBr—CH$_2$Br or CBr=CH$_2$ radical, and m is 0, and n is 1 or 2.

10. A compound according to claim 1, which compound contains one or more than one sulfo group.

11. A process for the preparation of the compound of formula (1) as claimed in claim 1, which comprises diazotising an amine of formula

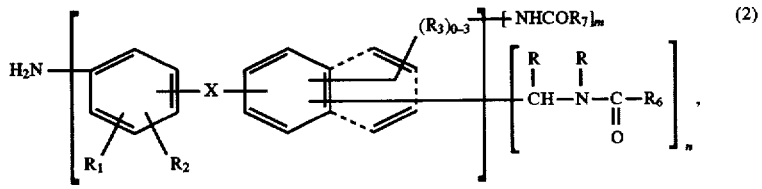

(2)

wherein $R_1$, $R_2$, $(R_3)_{0-3}$, $R_4$, $R_5$, $R_6$, $R_7$, X, n and m each have the meaning claimed in claim 1, and coupling the diazonium compound so obtained with a coupling component of formula

K-H  (3), wherein K is as claimed in claim 1.

12. A process for dyeing or printing a nitrogen-containing or hydroxyl group-containing fibre material, which comprises contacting said fibre material in an aqueous dyebath with a compound of formula (1) as claimed in claim 1.

13. A process according to claim 12 for dyeing or printing a wool-containing fibre material.

* * * * *